(12) United States Patent
Moriya et al.

(10) Patent No.: US 7,911,610 B2
(45) Date of Patent: Mar. 22, 2011

(54) OPTICAL MEASURING DEVICE

(75) Inventors: Naoji Moriya, Kyoto (JP); Yuzo Nagumo, Kyoto (JP); Yukihisa Wada, Kyoto (JP); Naofumi Sakauchi, Kyoto (JP); Fujio Inoue, Kyoto (JP); Masahiro Takebe, Kyoto (JP); Kenji Takubo, Kyoto (JP); Shinichiro Totoki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 341 days.

(21) Appl. No.: 11/996,057

(22) PCT Filed: Jan. 17, 2006

(86) PCT No.: PCT/JP2006/300540
§ 371 (c)(1),
(2), (4) Date: Jun. 18, 2008

(87) PCT Pub. No.: WO2007/010639
PCT Pub. Date: Jan. 25, 2007

(65) Prior Publication Data
US 2009/0251695 A1     Oct. 8, 2009

(30) Foreign Application Priority Data

Jul. 20, 2005  (JP) ................................ 2005-210672
Jul. 20, 2005  (JP) ................................ 2005-210673

(51) Int. Cl.
*G01N 21/00*   (2006.01)

(52) U.S. Cl. ........................................ 356/338; 356/337
(58) Field of Classification Search ........... 356/337–342
See application file for complete search history.

(56) References Cited

U.S. PATENT DOCUMENTS

| 6,091,492 A * | 7/2000 | Strickland et al. ............. 356/336 |
| 6,236,458 B1 * | 5/2001 | Igushi et al. ................... 356/336 |
| 2008/0221711 A1 * | 9/2008 | Trainer ........................... 700/54 |

FOREIGN PATENT DOCUMENTS
JP         2004-085528 A      3/2004

* cited by examiner

*Primary Examiner* — Michael P Stafira
(74) *Attorney, Agent, or Firm* — Cheng Law Group, PLLC

(57) ABSTRACT

The present invention relates to an optical measuring device which includes container for storing a sample, and an electrode pair for generating an electric field distribution upon impression of a voltage by an electrical power supply, thereby generating or extinguishing diffraction grating formed by a density modulation of particles within the sample. The particles within the sample are evaluated based upon a temporal change of an intensity of a diffracted light beam obtained by irradiating a light beam upon the diffraction grating formed by the density modulation of the particles. The electrodes constituting the electrode pair are configured to have a comb-like electrode teeth that are parallel with each other and are arranged such that the electrode teeth of one electrode are inserted between the electrode teeth of the other electrode. From such configuration, an optical measuring device of a high sensitivity and excellent S/N ratio can be obtained.

7 Claims, 17 Drawing Sheets

OPTICAL MEASURING DEVICE

TECHNICAL FIELD

The present invention relates to an optical measuring device which uses an optical method to measure information upon a diffusion of particles within a sample where the particles are movably dispersed within a medium, and more particularly relates to an optical measuring device which measures information upon a diffusion of particles present in a liquid or a gel by means of transient diffraction grating formed by a density modulation of the particles.

The optical measuring device according to present invention can also be applied to a measurement of the diameter of particles based upon a result of a measurement of a diffusion coefficient in the biotechnology, the fields of materials development, and the like.

BACKGROUND ART

There is the transient diffraction grating method as one of methods used to measure information upon diffusion of particles. For example, Patent Document 1 discloses a method to measure a diffusion constant by means of the transient diffraction grating method, thereby detecting protein association based upon a change of the diffusion constant.

According to the conventional transient diffraction grating method, two pulse excitation light beams with the same wavelength are irradiated upon a sample such that the beams cross each other, thereby forming interference fringes within the sample. While molecules (particles) in the sample present in bright portions of the interference fringes formed by the pulse excitation light beams are photoexcited, molecules (particles) in the sample present in dark portions of the interference fringes are not photoexcited, the photoexcited molecules and non-photoexcited molecules are alternately present in a regular arrangement in an area where the interference fringes are formed. If the diffusion coefficient of excited state is different from non-excited, and diffraction grating (transient diffraction grating) is temporarily generated in their diffusion process.

Also, in case molecules that have photochemical reactivity with target molecules are mixed with, reaction occur in bright portions in the fringe. Reacted molecules should have smaller diffusion coefficient, transition grating is generate in their diffusion process.

When a probe light beam is additionally irradiated upon the area where the transient diffraction gratins are formed, the probe light beam is diffracted by the transient diffraction grating. After the photo excitation process is occurred, the molecules that has smaller diffusion coefficient are diffuse more rapidly than molecules in another state. The transient diffraction grating is formed in the first diffusion process, and is extinguished in the second diffusion process, which is caused by the molecules that has larger diffusion coefficient, grating and an intensity of diffracted light beams generated from the probe light beam by the transient diffraction grating appear and vanish. On this occasion, a decay curve or raising curve of the intensity of the diffracted light beam represents two diffusion constants (diffusion coefficients) of the molecules with each state in the sample, and it is thus possible to calculate the diffusion coefficients of the molecules in the sample based upon the obtained curves, and to further obtain information on a size (particle diameter), a shape, and interaction with a solvent of the particles in the sample based upon the diffusion coefficient.

Moreover, as a method used to measure information upon a diffusion of particles, the inventors of the present invention propose such a device and a method that an electrode pair in a comb shape configured by electrically connecting one ends of multiple electrode teeth is arranged in a container storing a sample having particles dispersed in a medium such that the other ends of the electrode teeth of the respective electrodes are opposed to each other at a minute interval, a voltage is impressed upon the electrode pair to generate a regularly arranged electric field between the electrode teeth opposing to each other, a phoretic force thus acts upon the particles in the sample in the container to generate diffraction grating formed by a density modulation of the particles, after the generation of the diffraction grating, the impression of the voltage upon the electrode pair is stopped to diffuse the particles thereby extinguishing the diffraction grating, there is simultaneously detected an intensity of a diffracted light beam obtained by irradiating a light beam upon a portion where the diffraction grating are generated in the container, and information on the diffusion of the particles in the sample is evaluated based upon a temporal change of the intensity of the diffracted light beam in the extinction process of the diffraction grating.

[Patent Document] Japanese Patent Laid-Open Publication No. 2004-85528

DISCLOSURE OF THE INVENTION

Problems to be Solved by the Invention

According to the transient diffraction grating method among the conventional methods used to measure the information on the particle diffusion, since, in order to cross the two excitation light beams with the same wavelength to generate interfere fringes, the two excitation light beams whose optical path lengths are set to almost similar are lead to the area to be measured, and a probe light beam with a certain incident angle is made incident to the diffraction grating formed by the generated interference fringes. It is thus necessary to cause the two excitation light beams and the one probe light beam to cross at one point to be measured, and thus to adjust three optical axes of the excitation light beams and the probe light beam, and adjustment thereof thus becomes difficult.

As the excitation light beam used when molecules (particles) such as protein are used as the sample, it is necessary to employ a large laser light source with a short wavelength such as an excimer laser light source, and the size of the apparatus thus increases. Moreover, when the molecules (particles) such as protein are used as the sample, the protein molecules (particles) themselves do not generally show changes in the refractive index, the absorption coefficient, and the diffusion coefficient due to the excitation light beams, and it is thus necessary to label the sample material by a reagent (fluorescent reagent) which is to be photoexcited. However, attributes and properties of the protein molecules (particles) to be measured may change due to the labeling of the sample. Moreover, the labeling is generally an irreversible reaction, the molecules (particles) in the sample may be destructed, the measurement cannot thus be repeated with the same sample, and the molecules (particles) cannot be recovered to be used for other purposes. Moreover, the photoexcitation used to form the transient diffraction grating is generally irreversible reaction, and if a sample is once measured, the sample subsequently generates only a weak signal, and there poses such a problem that the measurement cannot be repeated.

Moreover, when particles other than molecules such as protein which can be easily labeled are used as the sample, some material may not be labeled, photoexcitation of the particles by the excitation light beam may be difficult, and the measurement by means of the above-described transient diffraction grating may be difficult.

On the other hand, according to the method proposed by the inventors which obtains the information on a diffusion of particles in a medium based upon a temporal change of an intensity of a diffracted light beam during an extinction process of diffraction grating formed by electrically distributing the particles unevenly thereby generating a density modulation, it is not necessary to use excitation light beams, to adjust optical axes thereof, and to label the sample, and the sample can be measured and used again.

However, according to this method, the diffraction grating formed by the density modulation of the particles are generated between the distal ends of the electrode teeth opposing to each other, the distance between the distal ends of the electrode teeth is as long as some tens of micrometers, and proper diffraction grating are not formed if the distance exceeds this distance. As a result, the width of the diffraction grating (length of the grating) formed by the density modulation of the particles is as long as some tens of micrometers. On the other hand, it is necessary to irradiate a light beam upon at least tens of the grating in order to measure the intensity of a diffracted light beam, and thus to irradiate the light beam limited to some tens of micrometers in width and to some millimeters in length upon a required portion in order to irradiate the light beam upon only diffraction grating formed by the density modulation in consideration of the width of the diffraction grating (length of the grating) formed by the density modulation of the particles, and there thus poses a problem that an alignment thereof is difficult.

On the other hand, if the light beam is not restricted, namely a light flux with a circular cross section, for example, is irradiated upon an area including the diffraction grating formed by the density modulation of the particles, there is also detected diffracted light beams coming from diffraction grating formed by the electrode teeth disposed on both sides of the diffraction grating formed by the density modulation of the particles, thereby increasing unnecessary signals, resulting in another problem that the detection sensitivity decreases.

Moreover, according to this proposed method, the electrode teeth arranged regularly at a constant interval also generate diffracted light beams in addition to the diffraction grating formed by the density modulation of the particles, and emerging directions of the light beams diffracted by the electrode teeth coincide with emerging directions of the diffracted light beams generated by the diffraction grating formed by the density modulation of the particles. The temporal change of the intensity of the diffracted light beam due to the generation/extinction of the diffraction grating formed by the density modulation of the particles is measured as a sum with the strong diffracted light beam from the electrode teeth. An efficiency of diffraction of the diffraction grating formed by particles is generally low, and the intensity change of the diffracted light beam received by a photodetector from the diffraction grating formed by the density modulation of the particles is detected as a slight change in an amount of light of the received light with a large intensity of the diffracted light beam from the group of the electrode teeth as a background.

Upon this occasion, for the detection of the light beam, due to shot noise which unavoidably presents a statistical fluctuation according to the square of the number of photons, if the intensity of the background light is strong, it is difficult to detect the small change in the amount of light, and there thus poses a problem that it is difficult to increase the S/N ratio of the measured result of the temporal change of the intensity of the diffracted light beam from the diffraction grating formed by the particles.

Moreover, according to the above proposed technology, the electrode pair used to generate the diffraction grating formed by the density modulation of the particles is formed upon an internal surface of the container storing the sample. If the container is a minute container which stores the sample in order to measure a minute amount, it is difficult clean the inside of the container. Further, according to this optical measuring method, since particles to be measured are forcedly captured in the vicinity of the electrodes to form areas with a high density of the particles, there may occur a phenomenon that the particles are attached to the vicinity of the electrodes.

If the container is not sufficiently cleaned after a measurement, and different particles are successively measured using the same container, there poses a problem that a measurement error possibly occur due to the contamination.

The present invention is devised in view of the foregoing problems, and has a first object to provide an optical measuring device which basically employs the method according to the above patent application by the present applicant which generates diffraction grating formed by a density modulation of particles, detects the intensity of a diffracted light beam during the extinction process thereof, and obtains information upon the diffusion of the particles, solves the problems of the conventional transient diffraction grating method, obtains more information on the diffracted light beam by the diffraction grating formed by the density modulation of the particles even if a general light flux such as that with an circular cross section is used without restricting the irradiated light beam, and increases the sensitivity of the measurement.

Moreover, a second object of the present invention is, in the same optical measuring device which employs the diffraction grating formed by the density modulation of the particles, to selectively measure the diffracted light beam from the diffraction grating formed by the density modulation of the particles without influence of a diffracted light beam from diffraction grating formed by electrode teeth, thereby increasing the S/N ratio thereof.

Further, a third object of the present invention is, in the same optical measuring device which employs the diffraction grating formed by the density modulation of the particles, to facilitate cleaning of a container which stores a sample and electrodes, thereby preventing a generation of a measurement error due to contamination.

Means for Solving the Problem

In order to attain the above first object, there is provided an optical measuring device according to a first aspect including a container that stores a sample of particles movably dispersed within a medium, an electric power supply that generates a voltage in a predetermined pattern including a DC, a frequency modulation, and a voltage modulation or in an pattern arbitrarily set, an electrode pair that is provided within the container, and generates an electric field distribution regularly arranged within the container upon impression of the voltage by the electric power supply, control means that controls the impression of the voltage upon the electrode pair from the electric power supply to generate/extinguish diffraction grating formed by a density modulation of the particles generated by a phoretic force acting upon the particles within the sample within the container, a light source that irradiates a light beam upon a generated portion of the diffraction grating within the container, and a photodetector that detects a diffracted light beam of the light beam diffracted by the diffraction grating, where the particles within the sample are evaluated based upon a temporal change of an intensity of the diffracted light beam detected by the photodetector, the respective electrodes constituting the electrode pair comprise multiple linear electrode teeth that are parallel with each other, and a connecting portion that electrically connects the respective electrode teeth with each other, and the respective electrodes are arranged such that while the electrode teeth of one of the electrodes are inserted between the electrode teeth of the other of the electrodes, the electrode teeth of the respective electrodes are separated by a constant interval, are parallel with each other, and are disposed alternately.

Moreover, an optical measuring device according to a second aspect attains the first and second objects at the same time, and is characterized by using the following electrode pair in place of the electrode pair according to the first aspect.

Namely, according to the electrode pair of the second aspect, the respective electrodes constituting the electrode pair include multiple linear electrode teeth that are parallel with each other, and a connecting portion that electrically connects the respective electrode teeth with each other, and are formed such that there are alternately arranged an electrode-tooth-concentrating area where at least two of the electrode teeth are arranged next to each other, and an electrode-tooth-absent area where no electrode tooth is present, and the respective electrodes are arranged such that the electrode-tooth-concentrating area of one of the electrodes is arranged in the electrode-tooth-absent area of the other electrode, and the electrode teeth of the respective electrodes are parallel with each other.

Moreover, an optical measuring device according to a third aspect attains the first and second objects at the same time, and is characterized by using the following electrode pair in place of the electrode pair according to the first aspect.

Namely, according to the electrode pair of the third aspect, the respective electrodes constituting the electrode pair include multiple linear electrode teeth that are parallel with each other, and a connecting portion that electrically connects the respective electrode teeth with each other, the respective electrodes are arranged such that while the electrode teeth of one of the electrodes are inserted between the electrode teeth of the other of the electrodes, the electrode teeth are arranged in parallel with each other, between the electrode teeth next to each other of the respective electrodes are the electrode tooth of the other of the electrodes as well as a floating electrode tooth that is not connected either of the electrodes, and has a shape approximately similar to the respective electrode teeth, and the floating electrode tooth and the electrode teeth of the respective electrodes are arranged at a constant interval to each other.

According to the respective aspects of the present invention, at least one electrode of the electrode pair is covered with a thin film in order to prevent the electrode from reacting to the sample within the container.

Moreover, in order to attain the above third object, there is provided an optical measuring device according to a fifth aspect including a container that stores a sample of particles movably dispersed within a medium, an electric power supply that generates a voltage in a predetermined pattern including a DC, a frequency modulation, and a voltage modulation or in an pattern arbitrarily set, an electrode pair that is provided within the container, and generates an electric field distribution regularly arranged within the container upon impression of the voltage by the electric power supply, control means that controls the impression of the voltage upon the electrode pair from the electric power supply to generate/extinguish diffraction grating formed by a density modulation of the particles generated by a phoretic force acting upon the particles within the sample within the container, a light source that irradiates a light beam upon a generated portion of the diffraction grating within the container, and a photodetector that detects a diffracted light beam of the light beam diffracted by the diffraction grating, where the particles within the sample are evaluated based upon a temporal change of an intensity of the diffracted light beam detected by the photodetector, a part of a wall of the container is formed with a material which transmits the light beam from the light source, the electrode pair is formed upon a structure which transmits the light beam from the light source, and the structure is detachably installed at a position corresponding to the wall of the container which transmits the light beam from the light source.

As a structure of the above container, there may be employed such a configuration (according to a sixth aspect) that the structure upon which the electrode pair is formed is detachably installed upon the container so as to constitute the part of the wall of the container which transmits the light beam from the light source.

Moreover, the container preferably employs such a configuration (according to a seventh aspect) that the container comprises a structure of a plurality members detachably assembled with each other in addition to the structure upon which the electrode pair is formed.

Moreover, it is preferable to employ such a configuration (according to an eighth aspect) that an engaging mechanism is formed between the container and the structure upon which the electrode pair is formed in order to maintain a mutual positional relationship thereof upon the structure upon which the electrode pair is formed being installed upon the container.

Moreover, the present invention may employ such a configuration (according to ninth aspect) that, in order to maintain a mutual positional relationship between the structure upon which the electrode pair is formed and an optical path of the light beam emitted from the light source, there is formed an engaging mechanism between either of the structure or the container and a holding member that holds either of the structure or the container within the optical measuring device.

The inventions according to the first to fourth aspects improve the above proposed technology which electrophoreses the particles dispersed in the sample in the container by impressing a voltage upon the electrode pair provided within the container, generates/extinguishes the diffraction grating formed by the density modulation of the particles, and obtains the information upon the diffusion of the particles based upon the temporal change of the intensity of the diffracted light beam in the extinction process, and attain the first object not by arranging the electrode teeth formed upon the respective electrodes constituting the electrode pair opposing to each other with a minute gap, and generating diffraction grating formed by the density modulation of the particles therebetween, but by arranging the linear electrode teeth formed upon the one electrode so as to be inserted between the electrode teeth formed upon the other electrode, and thus generating a diffraction grating formed by the density modulation of the particles along the lengthwise direction of the respective linear electrode teeth.

Namely, when an AC or DC voltage is impressed between the respective electrodes while the respective electrode teeth of the one electrode are inserted between the electrode teeth of the other electrode, areas with a high density of the particles formed by a cyclic electric field generated by the electrode pair are present between the electrode tooth of the one electrode and the electrode tooth of the other electrode, which are next to each other, and along these electrode teeth. Namely, a width of the diffraction grating (length of the grating) formed by the density modulation of the particles is approximately the same as an interdigital length of the electrode teeth of the respective electrodes. As a result, even if the light beam being irradiated upon the diffraction grating formed by the density modulation of the particles is a light flux with a circular cross section, for example, a component corresponding to the diffracted light beam which is a part of obtained entire diffracted light beam, and comes from the diffraction grating formed by the density modulation of the particles increases by an amount corresponding to an increased amount of the width of the diffraction grating compared with the proposed prior art, resulting in an increase of the sensitivity of the measurement.

Moreover, the inventions according to the second and third aspects are intended to additionally attain the second object by making the interval of the diffraction grating formed by the electrode teeth and the interval of the diffraction grating formed by the density modulation of the particles different from each other.

Namely, according to the invention of the second aspect, although the electrode teeth of the respective electrodes are not arranged alternately as described above, and the electrode teeth of the respective electrodes are not arranged at a constant interval, there are alternately formed the electrode-tooth-concentrating areas where at least two of the electrode teeth are formed next to each other, and the electrode-tooth-absent areas where no electrode tooth is present, and there is provided the arrangement that at least two of the electrode teeth of the one electrode are inserted into the electrode-tooth-absent area of the other electrode. With this configuration, areas with a high density of the particles generated by an electric field distribution formed by the impression of a voltage upon the electrode pair are formed only at positions where the electrode tooth of the one electrode and the electrode tooth of the other electrode are next to each other, and the grating interval of the diffraction grating formed by the density modulation of the particles is wider than the interval of the respective electrode teeth. With this configuration, an emerging direction of a [2 m+1]th (m is an integer) diffracted light beam of the diffracted light beams coming from the diffraction grating formed by the density modulation of the particles can be made different from an emerging direction of a diffracted light beam coming from the diffraction grating formed by the electrode teeth, and it is thus possible to selectively detect the diffracted light beam generated by the density modulation of the particles.

Moreover, according to the invention of the third aspect, although the electrode teeth of the respective electrodes are formed at a constant interval, and these electrode teeth of the respective electrodes are arranged alternately, between the electrode teeth next to each other of the respective electrodes are disposed the electrode tooth of the other electrode as well as the floating electrode (dummy electrode) in the shape similar to that of the respective electrode teeth, thereby providing an effect similar to the above configuration.

The invention according to the fourth aspect is intended to protect the electrodes of the above configurations, and at least an electrode which reacts to the particles and/or a disperse medium in the sample stored in the container is covered by the thin film providing the protective function to prevent the electrode from being eroded or oxidized, resulting in the electrode pair used for a long period.

According to the inventions of the fifth to ninth aspects, the electrodes, which generate an electric potential distribution in the container to generate/extinguish the diffraction grating formed by the density modulation of the particles, are not formed integrally with the container, which is used to store a liquid or gel sample with the particles dispersed in the medium, the electrodes are formed upon the structure which is independent of, and detachable from the container, and the structure upon which the electrode pair is formed is removed from the container for cleaning, resulting in easy and sufficient cleaning.

Moreover, the relationship between the structure upon which the electrode pair is formed and the container may be such a detachable structure that the structure is inserted into and fixed to the container as well as a structure that the structure upon which the electrode pair is formed forms a part of the wall of the container as disclosed by the invention according to the sixth aspect. Namely, the structure which practically achieves the function as the container when the structure is installed can provide the similar effect.

Moreover, as the structure of the container, there may be employed the undetachable structure as well as the structure where multiple members can be detachably assembled as disclosed by the invention according to the seventh aspect. This structure may be applied to both the configuration where the container is complete, and the structure is inserted into and fixed to the container or the like, and the configuration where the structure forms a part of the wall of the container.

For the configuration where the structure upon which the electrode pair is formed and the container are detachable from each other, in order to provide reproducibility of the positional relationship therebetween, it is effective to provide the configuration where the engaging mechanism is formed therebetween in order to attach them to each other always maintaining in the constant positional relationship as disclosed in the invention according to the eight aspect.

Moreover, according to the present invention, the position of the diffraction grating formed by the density modulation of the particles generated in the container depends on the position of the electrode pair, and it is thus preferable to always maintain the positional relationship between the position of the electrode pair, therefore the structure upon which the electrode pair is formed, and the light source irradiating the light beam (probe light beam) upon the diffraction grating. According to the invention of the ninth aspect, there is formed the engagement mechanism as described above between the structure or the container upon which the structure is installed and the holding member which holds the structure or the container in the device. As a result, there is always provided a constant relationship between the diffraction grating formed by the density modulation of the particles generated in the container and the optical path of the probe light beam with respect to the diffraction grating.

BRIEF DESCRIPTION OF THE DRAWINGS

FIGS. 16A and 16B are perspective views showing a specific structure of a container used for the embodiment of the present invention, in which FIG. 16A shows an attaching/detaching process of a structure 200 upon which the electrode pair is formed and a container main unit 10, and FIG. 16B shows a state where they are attached to each other;

FIGS. 18A and 18B are perspective views showing still another example of the structure of the container 1 used for the embodiment of the present invention, in which FIG. 18A shows the attaching/detaching process of the structure 200 and the container main unit 10, and FIG. 18B shows the state where they are attached to each other; and FIGS. 19A and 19B are perspective views showing an example where a container main unit 10 of the container 1 according to the embodiment of the present invention has a structure detachably assembled from multiple components, in which FIG. 19A shows an assembling process of the container main unit 10 and an attaching/detaching process of the structure 200, and FIG. 19B shows a completed state of the assembly/attachment.

EXPLANATION OF REFERENCE NUMERALS

Figure 1:
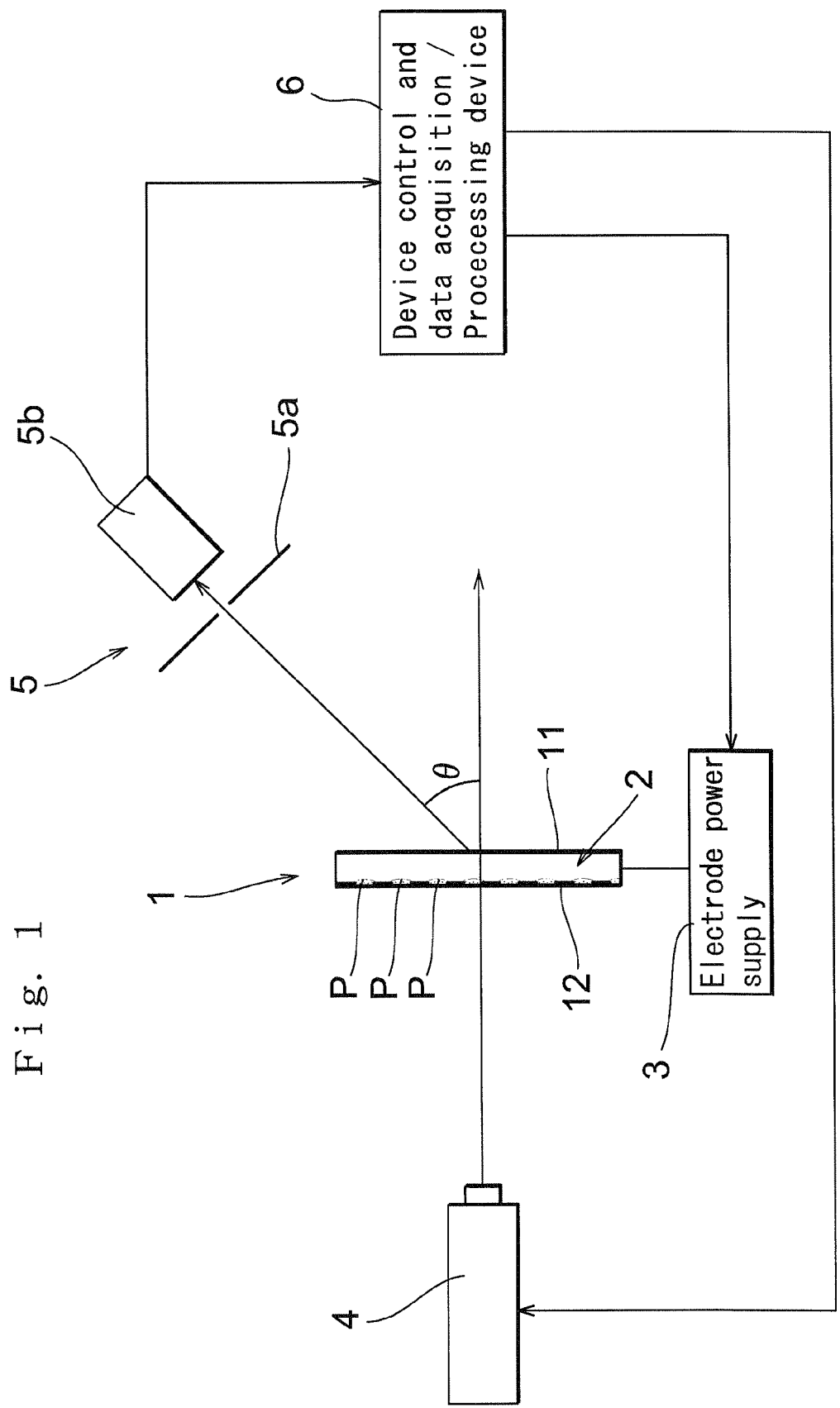
FIG. 1 is a configuration diagram according to an embodiment of the present invention including both a schematic diagram showing an optical configuration and a block diagram showing an electrical configuration.

1 Container
10 Container main unit
11, 12 walls made of a transparent material
2 Electrode pair
21, 22 Electrode
21*a*, 22*a* Electrode tooth
21*b*, 22*b* Connecting portion
23*a* Dummy electrode
3 Electrode power supply
4 Irradiation optical system
5 Detection optical system
6 Device control and data acquisition/processing device
100 Main unit portion
200 Structure on which electrode is formed
201 Groove

BEST MODE FOR CARRYING OUT THE INVENTION

A description will now be given of embodiments of the present invention with reference to drawings. It should be noted that the present invention is not limited to the following embodiments, and includes various forms without departing from the purpose of the present invention.

Figure 2:
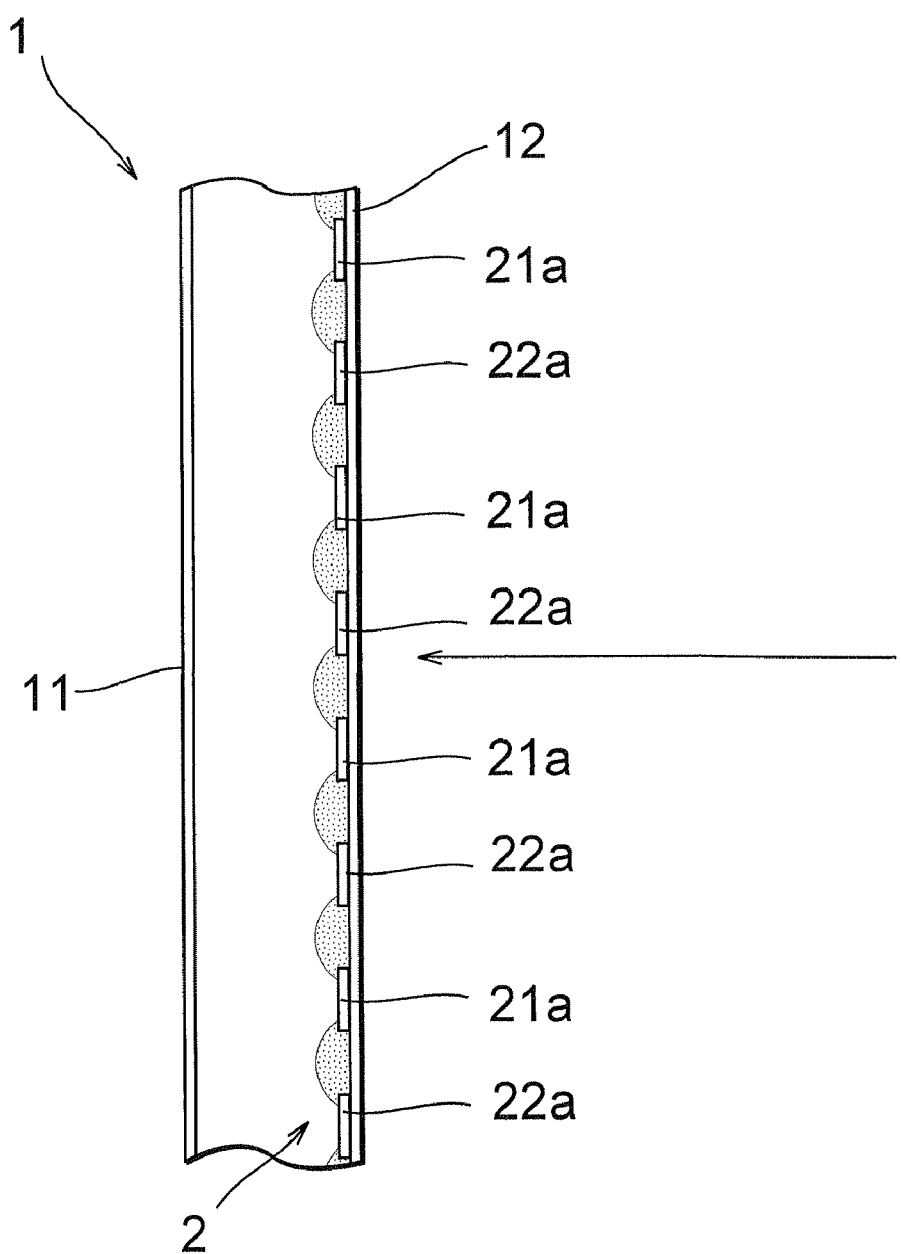
FIG. 2 is a partial schematic cross sectional view of a container 1 in FIG. 1.

FIG. 1 is a configuration diagram according to an embodiment of the present invention including both a schematic diagram showing an optical configuration and a block diagram showing an electrical configuration. FIG. 2 is a partial schematic cross sectional view of a container 1 in FIG. 1, and FIG. 3 is a diagram showing an example of a pattern of an electrode pair provided in the container 1 in FIG. 1.

As principle components, a device includes a container 1 which stores a sample having particles movably dispersed in a medium such as a sample having particles dispersed in a liquid or a sample having particles movably dispersed in a gel, an electrode power supply 3 which impresses a voltage upon an electrode pair 2 provided in the container 1, an irradiation optical system 4 which irradiates a light beam upon the container 1, a detection optical system 5 which measures a diffracted light beam from diffraction grating formed by a density modulation of particles in the container 1 upon the impression of the voltage upon the electrode pair 2, and a device control and data acquisition/processing device 6 which controls the entire device and receives and applies data processing to an output from the detection optical system 5.

The container 1 according to this example includes walls 11, 12 which are at least parallel with each other, and are respectively made of a transparent material, and the electrode pair 2 is formed upon a surface inside of one wall 12 as shown in FIG. 2.

Figure 3:
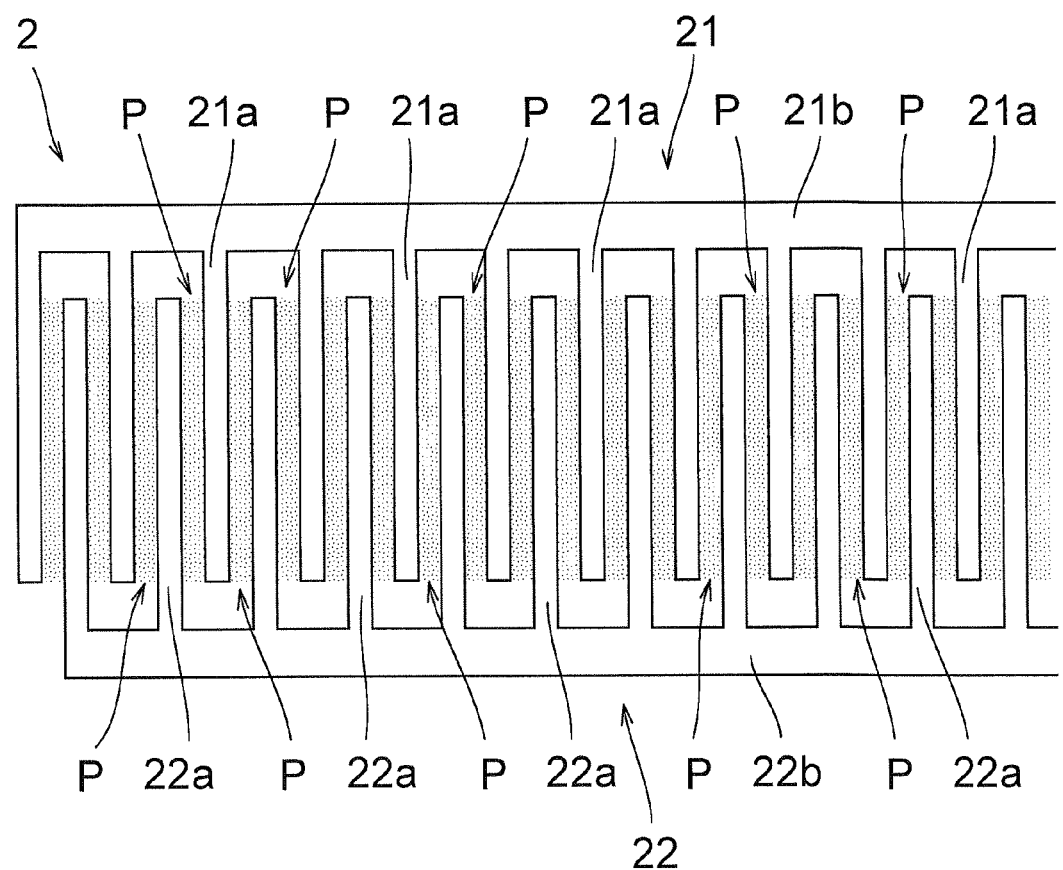
FIG. 3 is a diagram showing an example of a pattern of an electrode pair provided in the container 1 in FIG. 1.

The electrode pair 2 includes electrodes 21, 22 which respectively have a comb shape as shown in FIG. 3, the respective electrodes 21, 22 include multiple linear electrode teeth 21*a*, 22*a* which are parallel with each other, and connecting portions 21*b*, 22*b* which electrically connect the respective electrode teeth 21*a*, 22*a*. An interval between the respective electrode teeth 21*a*, 22*a* is the same, and the electrodes 21, 22 are arranged such that the electrode teeth 21*a* of the electrode 21 are inserted between the electrode teeth 22*a* of the electrode 22, namely the respective electrode teeth 21*a*, 22*a* of the electrodes 21, 22 interdigitate with each other alternately and in parallel by a certain length.

The electrode power supply 3 impresses the voltage upon the electrode pair 2, the impression of the voltage generates an electric field distribution within the sample stored in the container 1, and the electric field distribution electrophoreses the particles in the sample as described later, and a density modulation of the particles forms diffraction grating. The output voltage of the electrode power supply 3, namely the impressed voltage upon the electrode pair 2 is controlled by the device control and data acquisition/processing device 6 as described later.

The irradiation optical system 4 emits an approximately monochromatic light beam formed as an approximately parallel light flux, and the emitted light beam is irradiated upon a surface of the container 1 upon which the electrode pair 2 is formed. As a light source of the irradiation optical system 4, although a light source which emits only a monochromatic light beam such as a laser light source or an LED may be simply employed, there may be employed a light source which emits a quasi-monochromatic light beam obtained from a continuous-wavelength light source by means of a band-pass filter or a spectroscope, and the spectral bandwidth may be some tens of nanometers or less in a visible wavelength region, for example.

The detection optical system 5 is disposed in a direction in which a light beam diffracted by the diffraction grating formed by the density modulation of the particles in the container 1, first-order diffracted light beam, for example, among the light beams from the irradiation optical system 4 is emitted. The detection optical system 5 is constituted by a pin hole 5a and a photodetector 5b, for example. The detection optical system 5 measures a temporal change in an intensity of the diffracted light beam by the diffraction grating formed by the density modulation of the particles in the container 1.

When an AC voltage is impressed between the respective electrodes 21, 22 constituting the electrode pair 2 within the above configuration, the distribution of the electric field is formed within the sample within the container 1 corresponding to an electrode pattern thereof, and the density modulation of the particles are generated by dielectrophoresis based upon the distribution of the electric field. Namely, according to the pattern of the electrode pair in FIG. 3, an area P with a high density of the particles is generated in each gap between the electrode tooth 21a of the electrode 21 and the electrode tooth 22a of the electrode 22. The high density areas P of the particles are formed in parallel with the electrode teeth 21a, 22a, and as a spatial repetition in the same pitch as an arrangement pitch of the electrode teeth 21a or 22a, and the multiple high density areas P of the particles form the diffraction grating. In the generated state of the diffraction grating, if the impression of the voltage upon the electrode pair 2 is stopped, for example, the diffusion of the particles starts, the spatial density of the particles in the sample becomes uniform, and the diffraction grating formed by the density modulation of the particles finally disappear.

Figure 4:
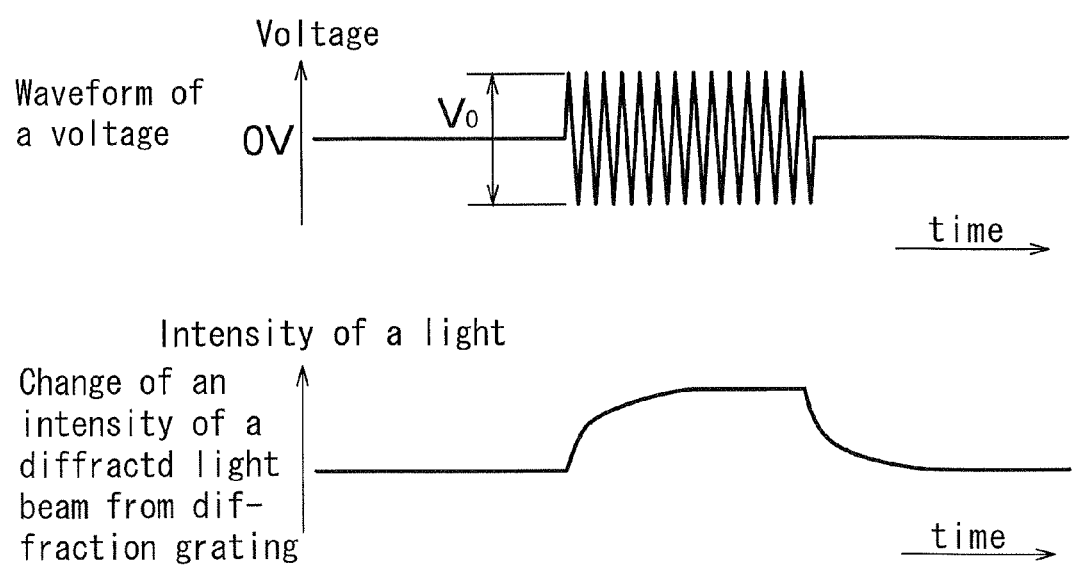
FIG. 4 is a diagram showing an example of temporal changes of a waveform of a voltage impressed upon an electrode pair 2 according to the embodiment of the present invention, and a temporal change of an intensity of a diffracted light beam from diffraction grating formed by the density modulation of particles.

If the light beam from the irradiation optical system 5 is irradiated upon the diffraction grating formed by the density modulation of the particles, the light beam is diffracted by the diffraction grating, and the intensity of the diffracted light beam gradually decreases as the diffraction grating disappear. FIG. 4 is a diagram showing an example of temporal changes of a waveform of the voltage impressed upon the electrode pair 2, and the temporal change of the intensity of the diffracted light beam by the diffraction grating formed by the density modulation of the particles. In this example, an AC voltage in a form of a sinusoidal wave with a peak-to-peak voltage of $V_o$ is impressed upon the electrode pair 2, a dielectrophoresis force acts upon the particles to generate the diffraction grating, and the impression of the voltage is stopped to stop the application of the dielectrophoresis force.

The temporal change of the intensity of the diffracted light beam during the extinction process of the diffraction grating formed by the density modulation of the particles depends on a diffusion coefficient of the particles, and it is possible to obtain information upon the diffusion of the particles in the sample such as the diffusion coefficient according to a measurement result of the temporal change. It is then possible to calculate the diameter of the particles from the diffusion coefficient.

An especially notable point of the above embodiment is that the width of the diffraction grating formed by the density modulation of the particles is approximately as long as a portion where the respective electrode teeth 21a, 22a of the electrodes 21, 22 constituting the electrode pair 2 interdigitate with each other, and even if the light beam from the irradiation optical system 5 is a light flux with a circular cross section, it is possible to largely increase a component corresponding to the diffracted light beam which is included in an obtained entire diffracted light beam, and comes from the diffraction grating formed by the density modulation of the particles compared with the proposed conventional technology, thereby increasing the detection sensitivity.

Although as the electrode pair 2 is used the configuration that the electrode teeth 21a of the one electrode 21 and the electrode teeth 22a of the other electrode 22 are alternately arranged in the above embodiment, the interval of the diffraction grating formed by the density modulation of the particles and the interval of the diffraction grating formed by the respective electrode teeth 21a, 22a are the same, the emerging directions of the diffracted light beams generated by these respective diffraction grating coincide with each other, the temporal change of the intensity of the diffracted light beam caused by the generation/extinction of the diffraction grating formed by the density modulation of the particles is measured as a sum with the strong diffracted light beam caused by the electrode teeth, and there poses a problem in terms of the S/N ratio.

Figure 5:
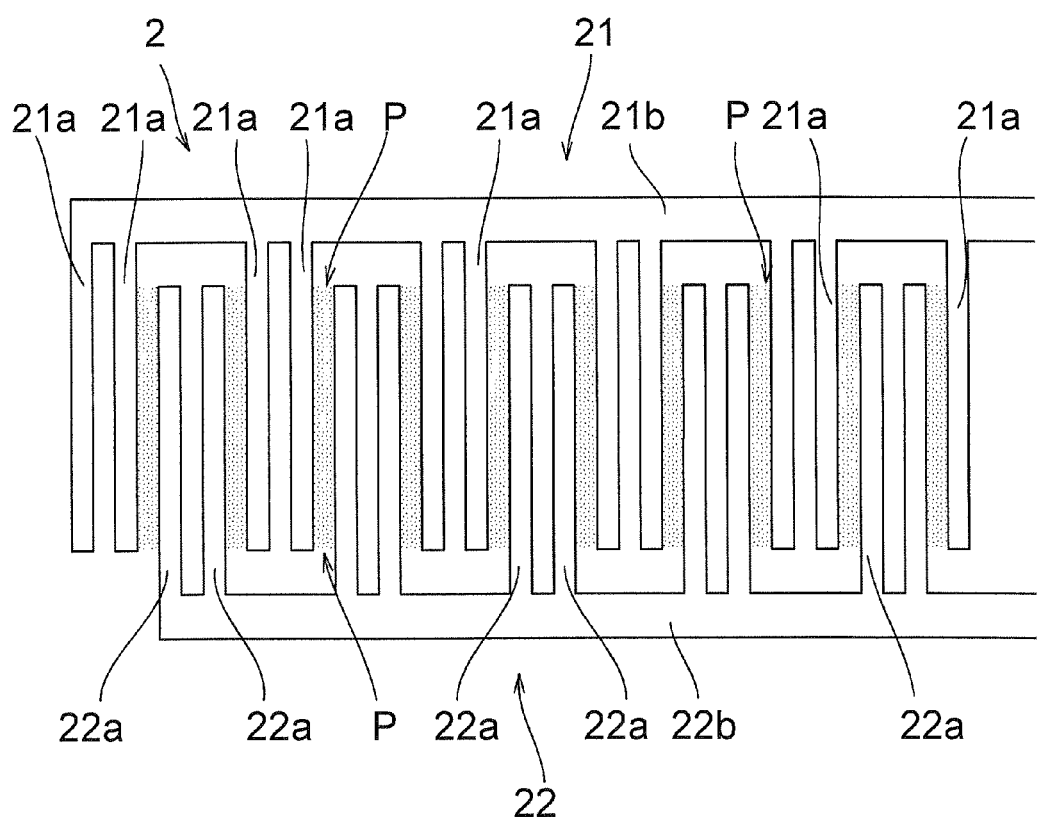
FIG. 5 is a diagram showing the pattern of the electrode pair according to another embodiment of the present invention.

FIG. 5 shows an example of a configuration of the electrode pair 2 used to solve this problem. According to the example shown in FIG. 5, the electrodes 21, 22 constituting the electrode pair 2 respectively have such a form that electrode-tooth-concentrating areas where two linear electrode teeth 21a or 22a are disposed next to each other, and electrode-tooth-absent areas where no electrode tooth is present are alternately formed. The two electrode teeth 21a or 22a in the one electrode-tooth-concentrating area are inserted into the other electrode-tooth-absent area, and there is thus provided an overall configuration where two of the respective electrode teeth 21a and 22a are alternately disposed in parallel with each other at a constant interval.

With the electrode pair 2 in this pattern, when a voltage is impressed between the electrodes 21 and 22, the high density areas P of the particles are formed only in areas where electrode teeth with polarities opposite to each other are next to each other, namely, the electrode tooth 21a of the one electrode 21 and the electrode tooth 22a of the other electrode 22 are next to each other as illustrated. Thus, the grating interval of the diffraction grating formed by the high density areas P of the particles is twice as wide as the grating interval of the diffraction grating formed by the electrode teeth 21a, 22a, resulting in a difference between both of grating constants. Of the diffracted light beams from the diffraction grating formed by the density modulation of the particles, diffracted light beams of specific orders determined by the grating constant of the diffraction grating formed by the density modulation appear in directions where the diffracted light beams generated by the diffraction grating formed by the electrode teeth are not present.

In the example shown in FIG. 5, a diffracted light beam of [2 m+1]th (m is an integer) order from the diffraction grating formed by the density modulation of the particles appears in the direction in which a diffracted light beam from the diffraction grating formed by the electrode teeth is not present, and if the detection optical system 5 is disposed in this direction, background light beams included in a light beam detected by the detection optical system 5 are only background light beams including scattered light beams, shot noise can be restrained to low, and it is possible to measure the diffracted light beam from the diffraction grating formed by the density modulation of the particles with an excellent S/N ratio.

Figure 6:
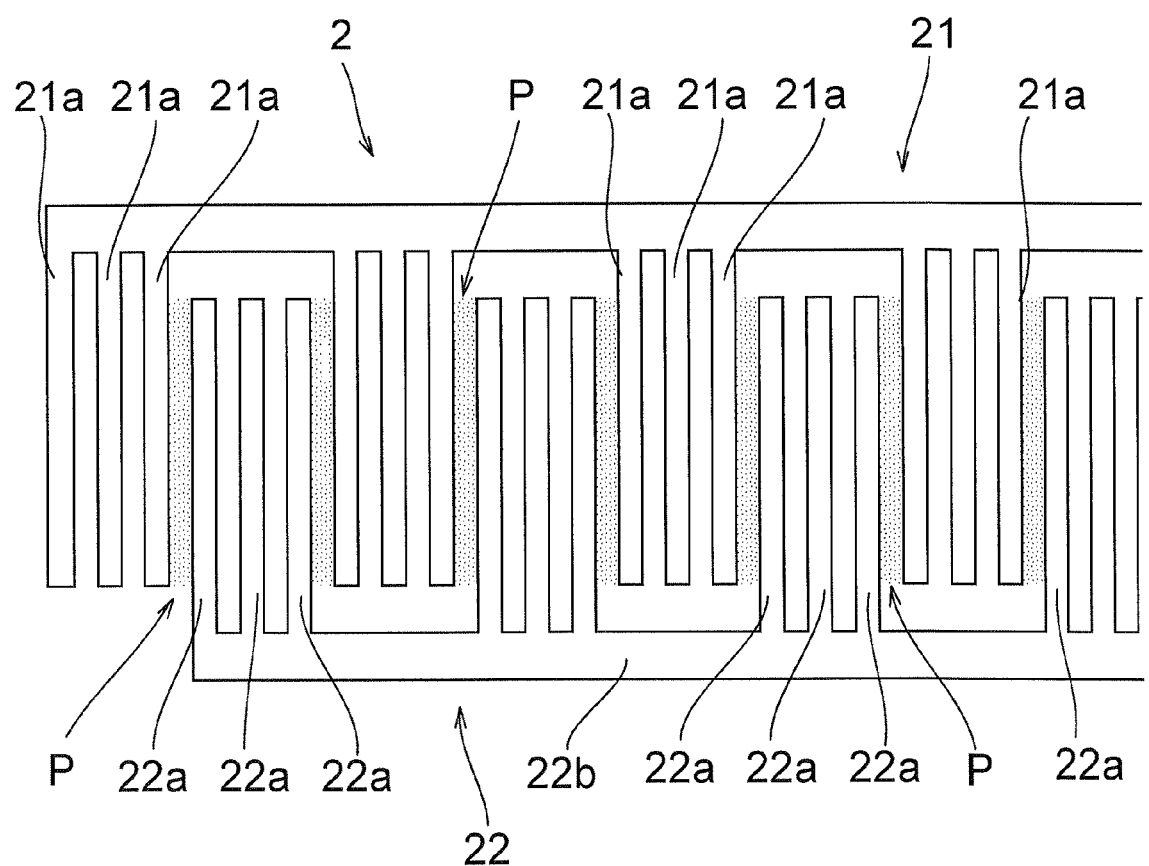
FIG. 6 is a diagram showing the pattern of the electrode pair according to still another embodiment of the present invention.

According to the above embodiment, although there is shown the example where two of the electrode teeth 21a, 22a of the respective electrodes 21, 22 are concentrated, the number of the concentrated electrode teeth is not limited to two, and three of the electrode teeth 21a, 22a of the respective electrodes 21, 22 may be concentrated as shown in FIG. 6, for example. In this case, the high density areas P of the particles are formed in a pitch three times as wide as the pitch of the electrode teeth 21a, 22a, and diffracted light beams of [3 m+1]th (m is an integer) order and [3 m+2]th order of diffracted light beams from the refraction grating formed by the high density areas P of the particles emerge in directions in which diffracted light beams from the diffraction grating formed by the electrode teeth are not present.

Figure 7:
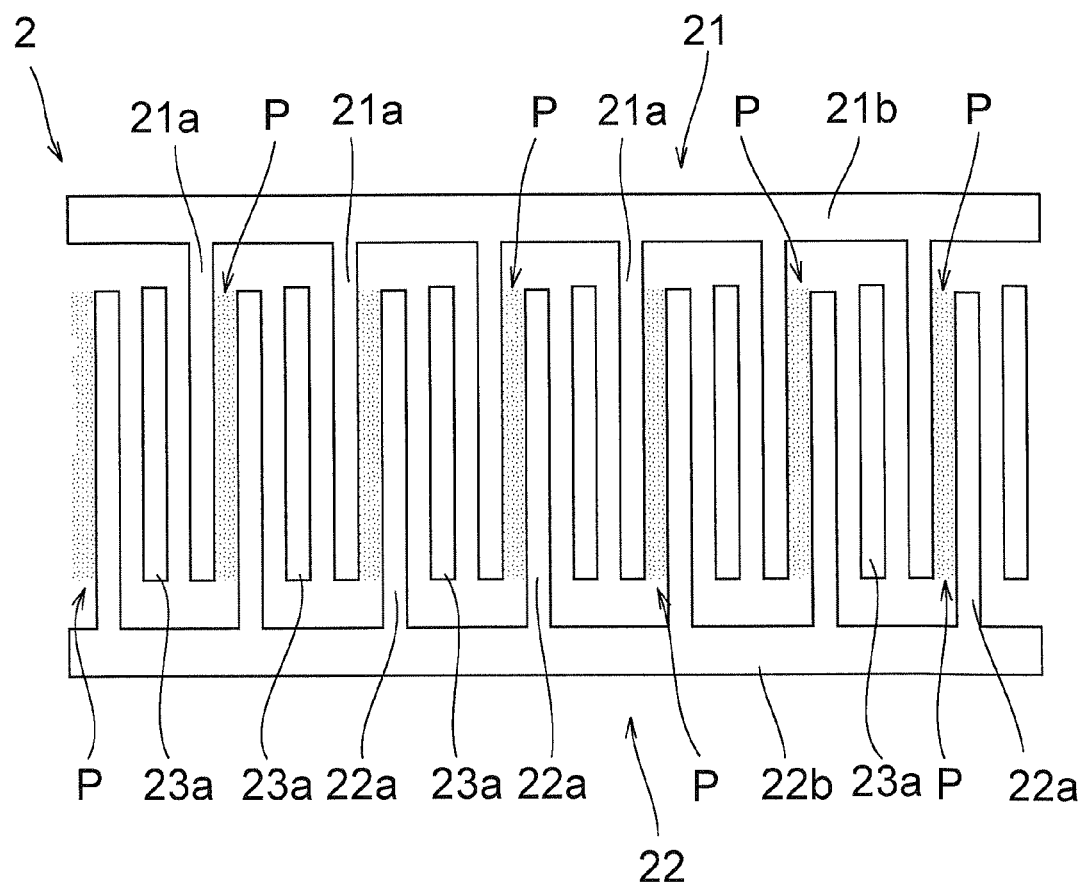
FIG. 7 is a diagram showing the pattern of the electrode pair according to yet another embodiment of the present invention.

Moreover, similar effects are provided if dummy electrodes 23a shown in FIG. 7 are used. The example shown in FIG. 7 is characterized in that both the electrode teeth 21a, 22a of the electrodes 21, 22 constituting the electrode pair 2 are formed at a constant interval, the respective electrodes 21, 22 are arranged such that these electrode teeth 21a, 22a are alternately present, between the electrode teeth 21a of the one electrode 21 are disposed the electrode tooth 22a of the other electrode 22 as well as the dummy electrode 23a which is not connected to either the electrode 21 or 22, and is electrically floating, and the dummy electrodes 23a and the electrode teeth 21a, 22a of the respective electrodes 21, 22 are arranged at a constant interval. When the electrode pair 2 in this pattern is used, the high density areas P of the particles are respectively formed only between the electrode teeth 21a and 22a, and the pitch of the high density areas P is three times as wide as the pitch of the electrode teeth 21a, 22a, and the dummy electrodes 23a as in the example in FIG. 6, and there are provided effects similar to those of the example in FIG. 6.

Moreover, if it is necessary to prevent electrons from directly received/supplied between the particles/liquid attracted by the electrode 21 or 22 and the electrodes 21, 22, thereby preventing the electrodes 21, 22 from being eroded or oxidized when an AC voltage with a superimposed offset voltage or a DC voltage is used as the voltage impressed upon the electrode pair 2 as described later, the electrode 21 and/or the electrode 22 may be covered by a thin film 10 having a protective function as exemplified in FIGS. 8 to 10. As a material of the thin film, there is preferably used $Ta_2O_5$ as a high dielectric constant film and $SiO_2$ as an insulation film.

Figure 8:
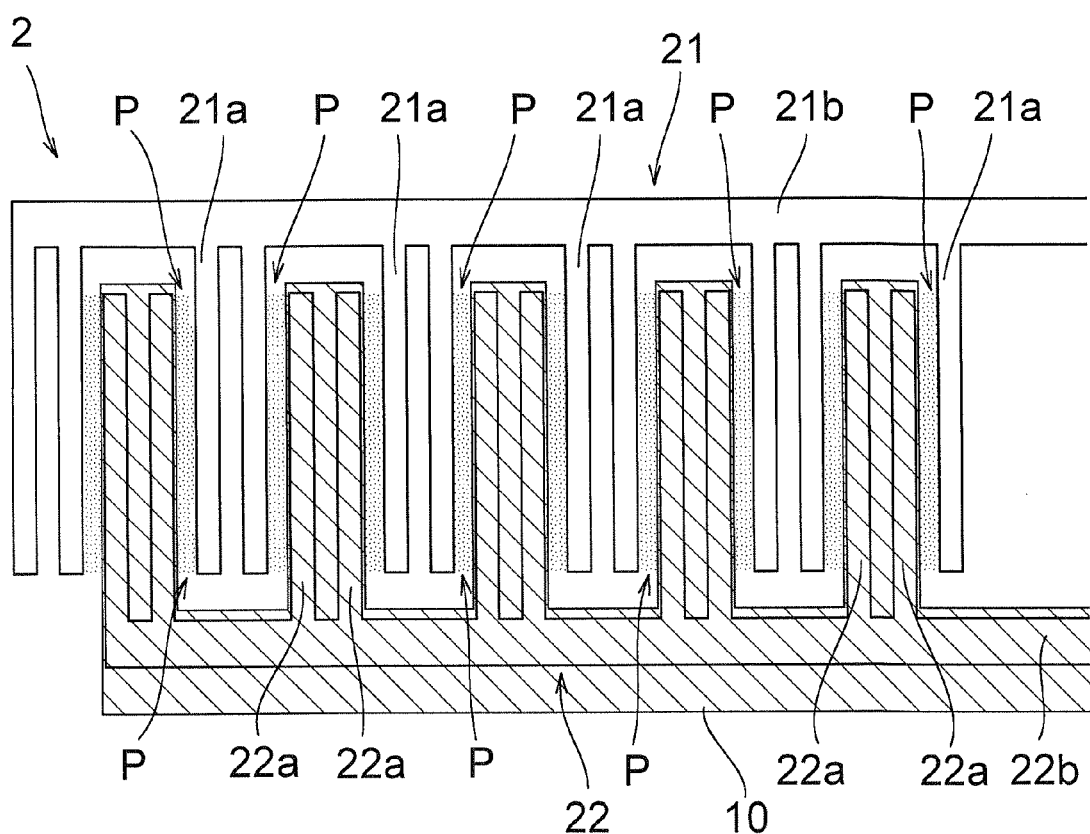
FIG. 8 is a diagram showing an example of a formation of a protection film for the electrode pair according to the respective embodiments of the present invention.
Figure 9:
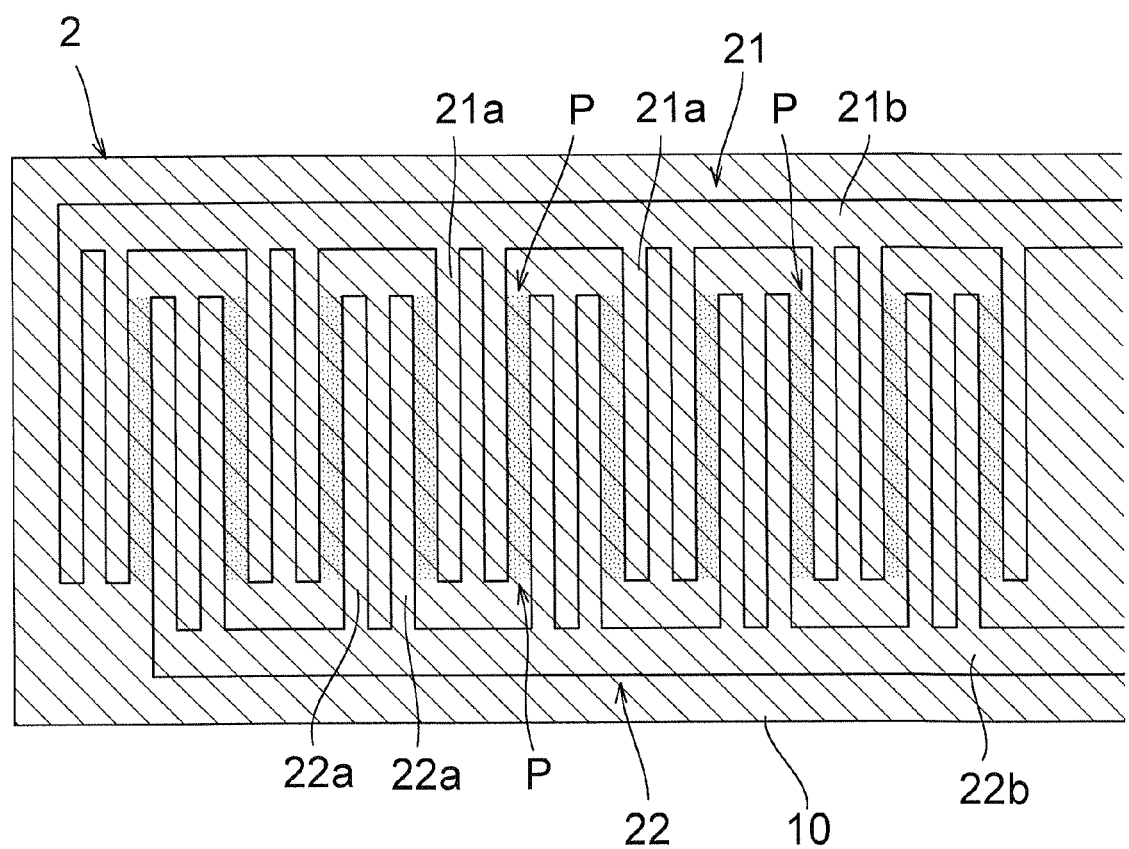
FIG. 9 is a diagram showing another example of the formation of the protection film for the electrode pair according to the respective embodiments of the present invention.
Figure 10:
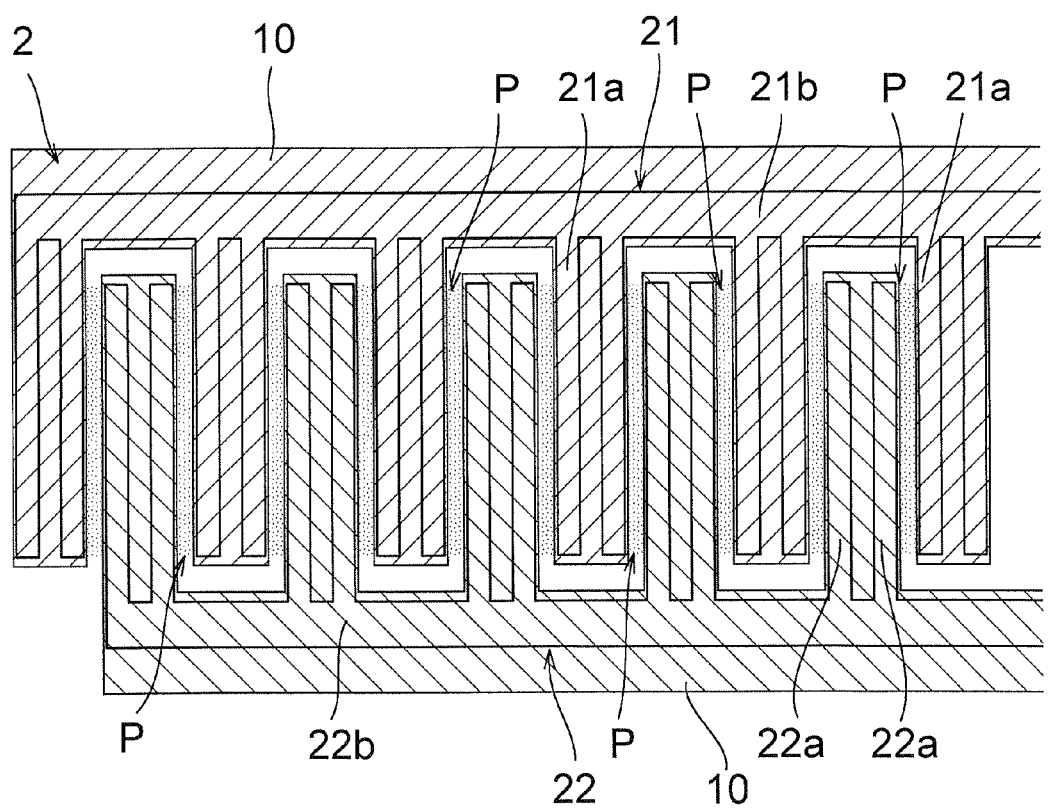
FIG. 10 is a diagram showing still another example of the formation of the protection film for the electrode pair according to the respective embodiments of the present invention.

FIG. 8 shows an example where only the one electrode 22 is covered with the thin film 10 having the protective function, FIG. 9 shows an example where the entire electrode pair 2 is covered with the thin film 10 having the protective function, and FIG. 10 shows an example where both the electrodes 21, 22 are respectively covered with the thin films 10 having the protective function.

The voltage impressed upon the electrode pair 2 is not limited to the sinusoidal AC voltage as described above, and the extinction of the diffraction grating formed by the density modulation of the particles generated by the impression of the voltage is not limited to the stoppage of the impression of the voltage as described above.

Figure 11:
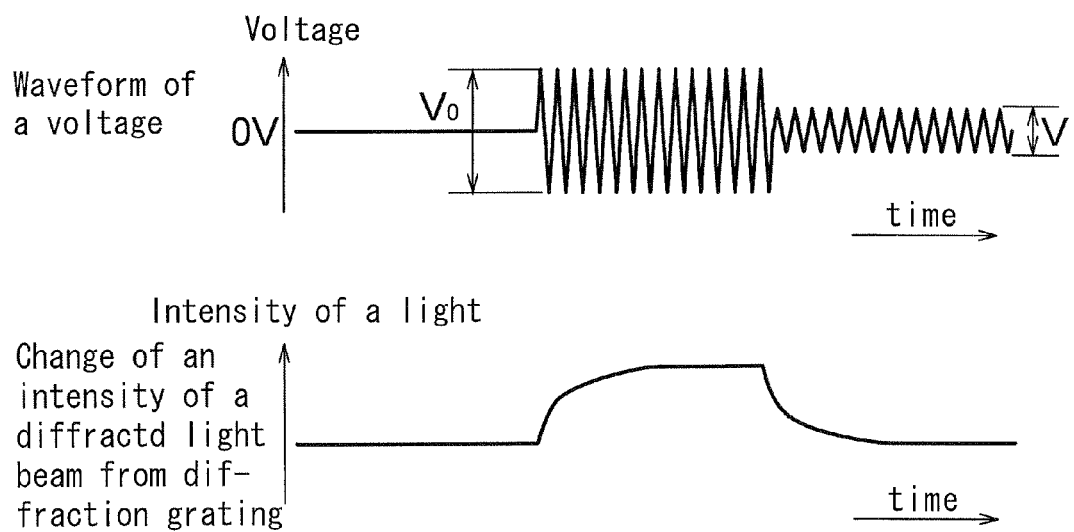
FIG. 11 is a diagram showing another example of the pattern of the voltage impressed upon the electrode pair according to the respective embodiments of the present invention.

Namely, as shown in FIG. 11, after a sinusoidal AC voltage, for example, is impressed upon the electrode pair 2 to generate the diffraction grating formed by the density modulation of the particles, it is possible to decrease the amplitude of the AC voltage from $V_o$ to V to extinguish the diffraction grating formed by the density modulation of the particles.

Figure 12:
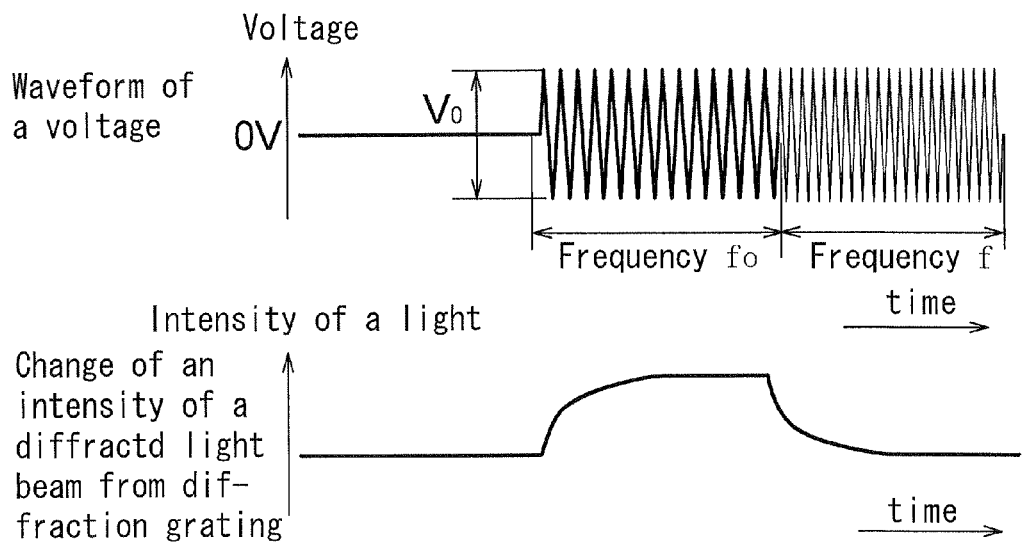
FIG. 12 is a diagram showing still another example of the pattern of the voltage impressed upon the electrode pair according to the respective embodiments of the present invention.

Moreover, a dielectrophoretic force depends on the frequency of the sinusoidal voltage, after a voltage with a frequency of $f_o$ which generates a large dielectrophoretic force is impressed upon the electrode pair 2 to generated the diffraction grating formed by the density modulation of the particles, the frequency is changed to a frequency f, which does not generate a dielectrophoretic force or generates a small dielectrophoretic force, to extinguish the diffraction grating formed by the density modulation of the particles as shown in FIG. 12.

Figure 13:
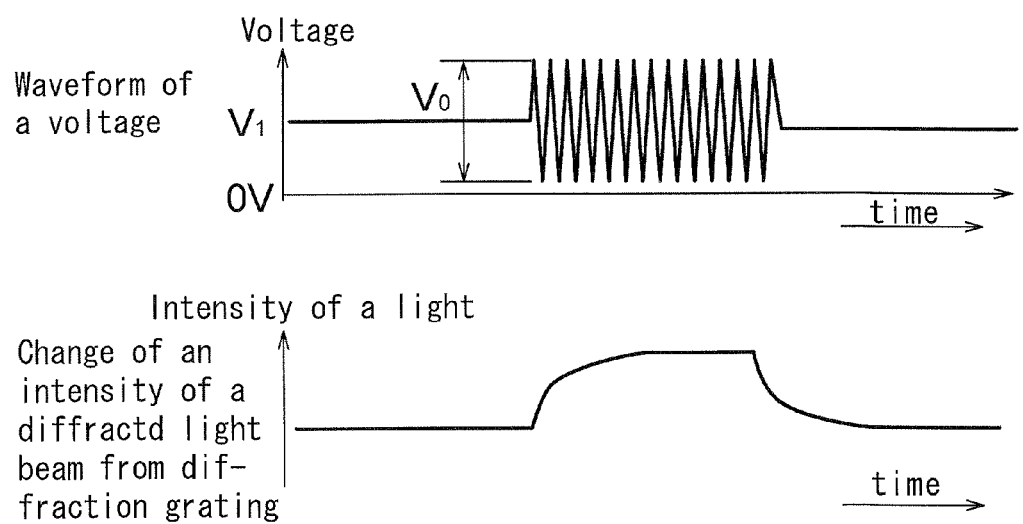
FIG. 13 is a diagram showing yet another example of the pattern of the voltage impressed upon the electrode pair according to the respective embodiments of the present invention.

Moreover, by superimposing an offset voltage $V_1$ upon a sinusoidal AC voltage as shown in FIG. 13, it is possible to attract and fix charged particles, which are more mobile than particles to be measured, on one electrode in advance, thereby limiting particles whose collection and diffusion are controlled by the dielectrophoresis to neutral particles.

Figure 14:
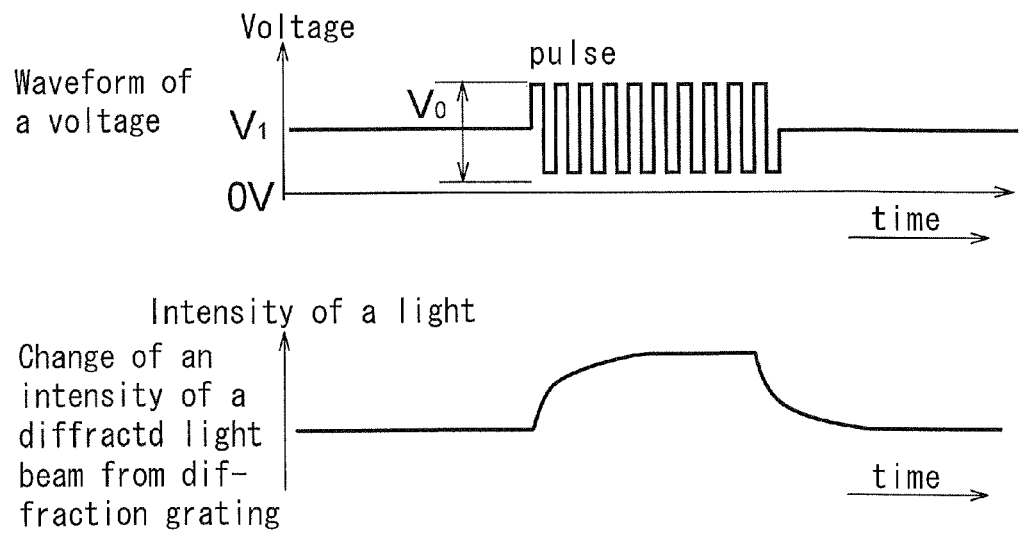
FIG. 14 is a diagram showing still yet another example of the pattern of the voltage impressed upon the electrode pair according to the respective embodiments of the present invention.

Further, the waveform of the voltage is not limited to the sinusoidal waveform, and a voltage in a pulse pattern generates a dielectrophoretic force independently of the pulse duty ratio as the sinusoidal voltage as shown in FIG. 14, and enables a measurement as in the above respective examples.

Figure 15:
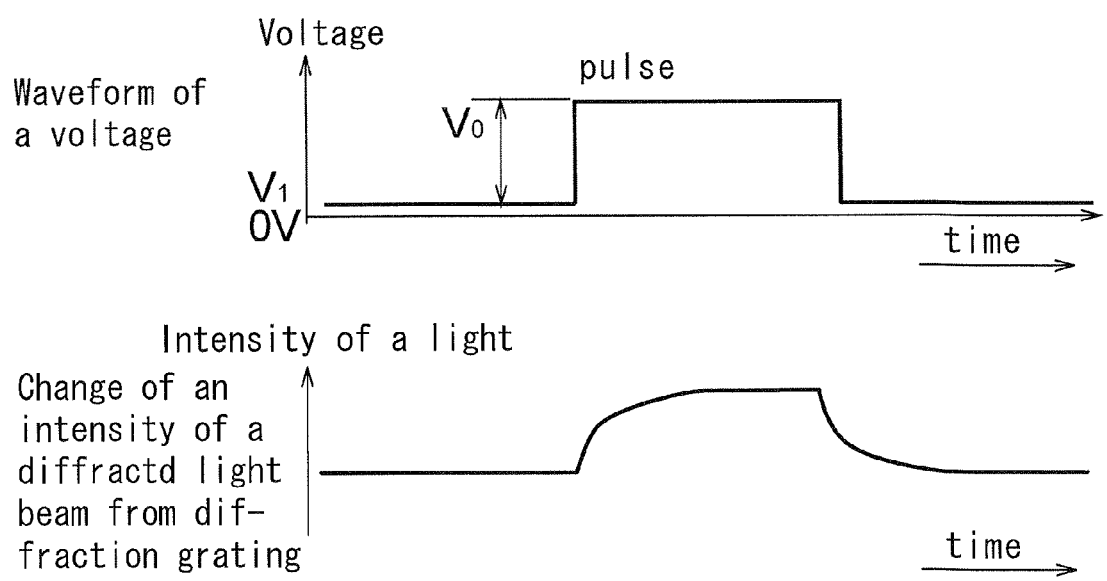
FIG. 15 is a diagram showing even still yet another example of the pattern of the voltage impressed upon the electrode pair according to the respective embodiments of the present invention.

Moreover, the phoretic force used in the present invention is not necessarily the dielectrophoretic force, and there may be used an electrophoretic phenomenon caused by impressing a DC voltage upon the electrode pair 2 as shown in FIG. 15, for example. In this case, an offset voltage $V_1$ may be superimposed upon a DC voltage $V_o$. Particles dispersed within a liquid and particles dispersed within a gel are somewhat charged, it is thus possible to collect the particles to form the high density areas P by means of the electrophoresis. When the DC voltage is impressed in this way or the offset voltage is superimposed upon the impressed voltage as shown in FIG. 13, in order to prevent electrons from being directly received/supplied between the charged particles attracted close to an electrode and the electrode, it may be necessary to cover the electrode with a protection film made of the above thin film having an insulation function.

Figure 16A:
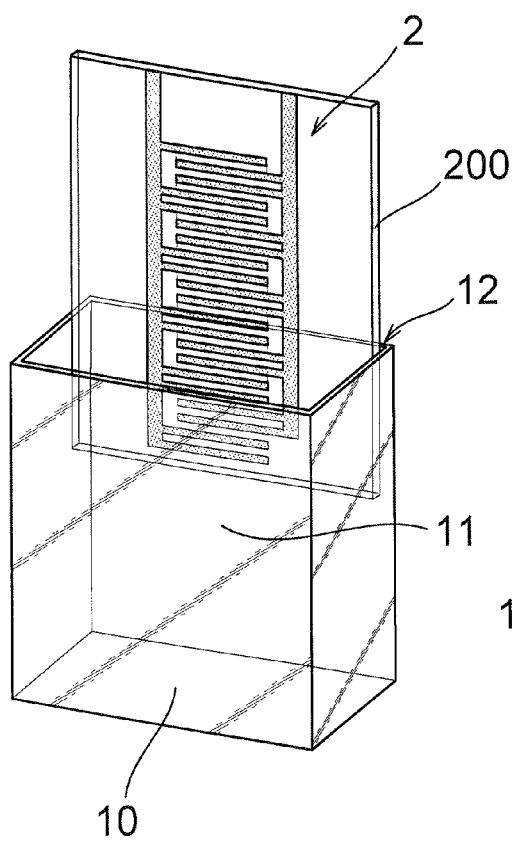
Figure 16B:
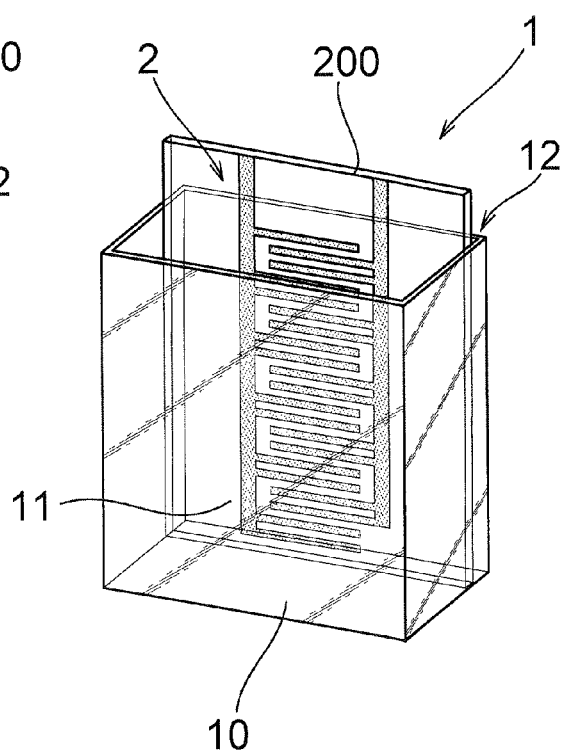

A description will now be given of a specific configuration of the container 1 used for the embodiment of the present invention. FIGS. 16A and 16B are perspective views showing the specific structure of the container 1. FIG. 16A shows an attaching/detaching process of a structure 200 upon which the electrode pair 2 is formed, and the container main unit 10, and FIG. 16B shows a state where they are attached to each other.

The container 1 is an assembly of the container main unit 10 and the structure 200 in a plate shape upon one surface of which the electrode pair 2 is formed, the container main unit 10 includes walls 11, 12 which are parallel with each other and are respectively made of a transparent material, and the container 1 has such a configuration that the structure 200 which is made of a transparent material in the plate shape, and the one surface of which the electrode pair 2 is formed is detachably inserted along the one wall 12 while the surface upon which the electrode pair 2 is formed is facing inside the container main unit 10.

It is preferable that grooves (not shown) with which the structure 200 is tightly engaged are formed upon the container main unit 10, thereby always installing the structure 200 in a certain positional relationship with the container main unit 10.

An especially notable point of the container structure is that the container 1 is constituted by the container main unit 10 and the structure 200 in the plate shape upon which the electrode pair 2 is formed, and the structure 200 is detachably installed upon the container main unit 10. As a result, after a measurement was carried out using the container 1, both the structure 200 and the container main unit 10 are independently cleaned while the structure 200 is detached from the container main unit 10, particles and the like can be certainly washed off from the container main unit 10 and the structure 200 after the measurement, thereby eliminating a cause of contamination in a subsequent measurement.

Figure 17:
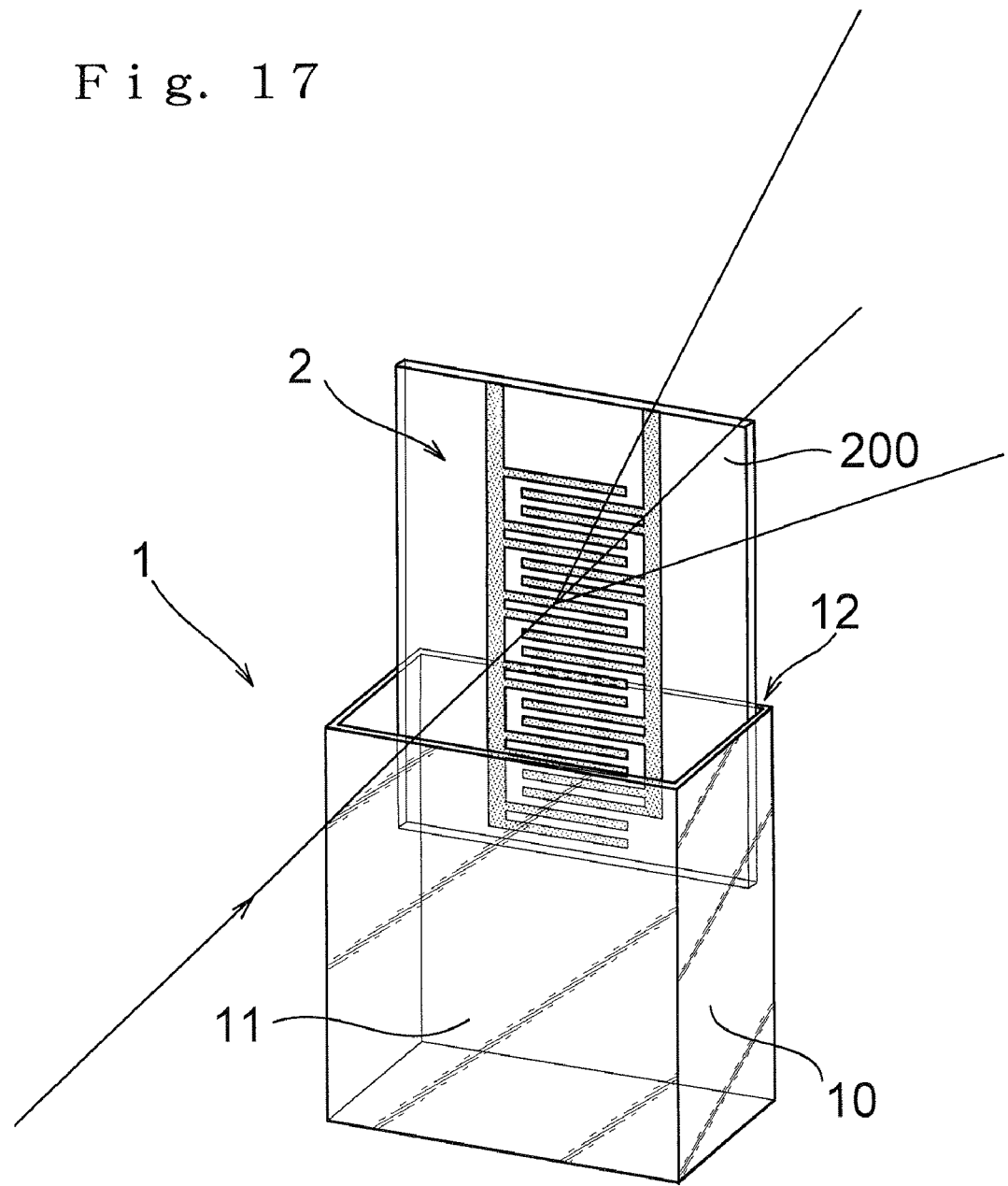
FIG. 17 is a perspective view showing another example of the container used for the embodiment of the present invention, and illustrating a case where there is employed a configuration which holds the structure 200 in a holding mechanism of a measuring device in a certain positional relationship with respect to an optical axis of an irradiation optical system 4.

In addition to the configuration that the structure 200 upon which the electrode pair 2 is formed is simply inserted into the container main unit 10, and the container main unit 10 is maintained in a certain positional relationship with the optical axis of the irradiation optical system 4 by means of a holding mechanism provided upon the measuring device, there may be provided such a configuration that the structure 200 is configured to be held by a holding mechanism of the measuring device in a certain positional relationship with the optical axis of the irradiation optical system 4, and the container main unit 10 is engaged over the structure 200 held by the holding mechanism as shown in FIG. 17.

Figure 18A:
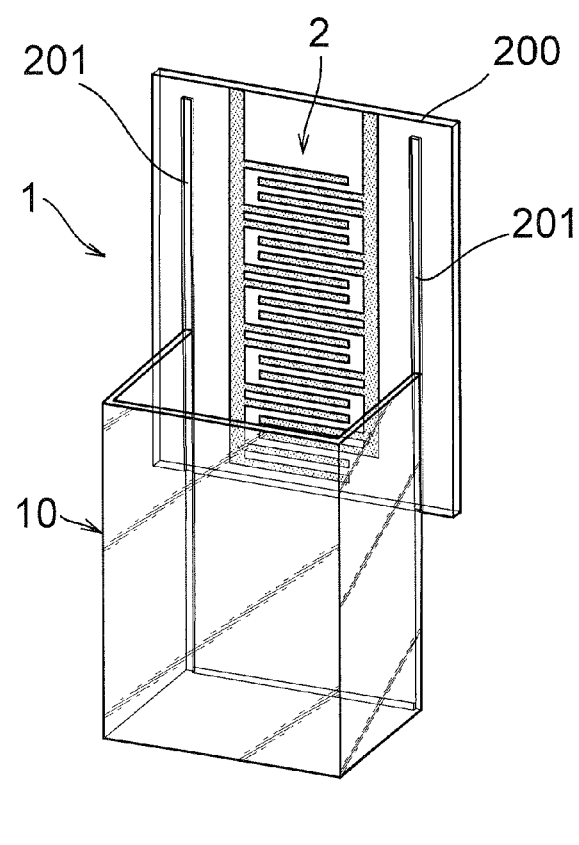
Figure 18B:
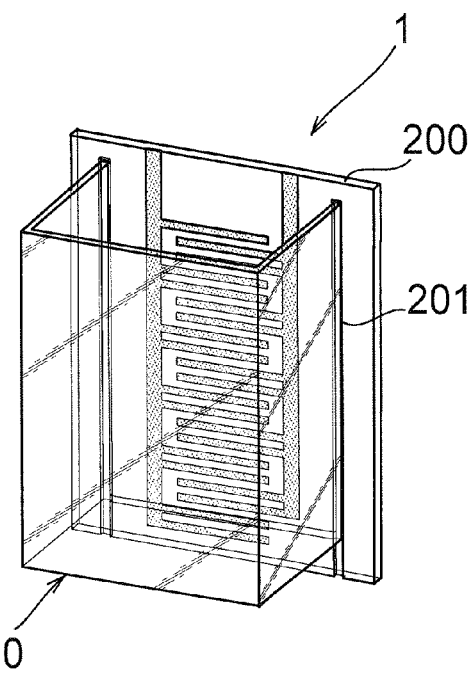

Moreover, although the above embodiment is configured such that the structure 200 upon which the electrode pair 2 is formed is inserted inside the container main unit 10, there may be employed such a structure that the structure 200 forms a part of the wall of the container 1, an attaching/detaching process of which is shown in FIG. 18A, and an installed state of which is shown in FIG. 18B.

Namely, in this example, the container main unit 10 has a cross section in a U shape formed by removing the wall 12 of the walls 11 and 12, which are parallel with each other, and are made of the transparent material, of the container main unit 10 of the above embodiment, and when the structure 200 is installed, the structure 200 practically forms the wall 12 of the above embodiment. Upon the structure 200 are formed grooves 201 which are to be engaged with the container main unit 10, and the structure 200 and the main unit 10 are always attached to each other in a certain positional relationship by inserting the container main unit 10 along these grooves 201.

It should be noted that when this configuration is employed, in the engaging portion between the container main unit 10 and the structure 200 is interposed a sealing component such as a packing if necessary. Moreover, when this configuration is employed, a structure which mutually integrates the container main unit 10 and the structure 200 with each other by means of a clip mechanism, a band, or the like may facilitate handling thereof.

Figure 19A:
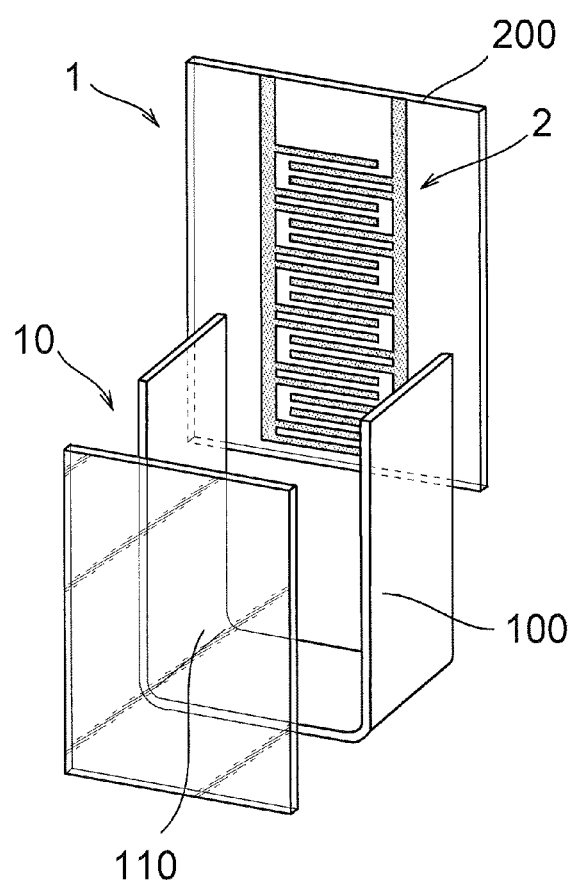
Figure 19B:
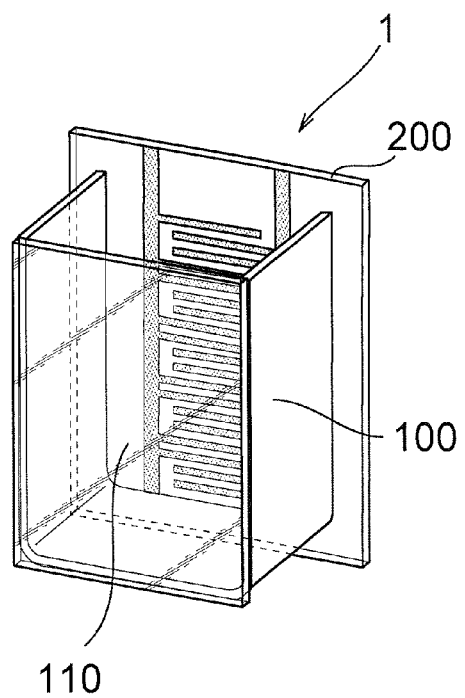

Moreover, there may be employed such a configuration that the container main unit 10 is detachably assembled from multiple members. FIGS. 19A and 19B show an example thereof. FIG. 19A shows an assembling/attaching process of the container main unit 10 and the structure 200, and FIG. 19B shows a completed state of the assembly/attachment.

In this example, the container 1 is formed by the container main unit 10 including a wall 110 which is in a plate shape made of a transparent material and a main unit portion 100 which is made of an arbitrary material in an approximately U shape and forms both side walls and a bottom plate, and the structure 200 in a shape of a plate which is made of a transparent material, and upon which the electrode pair 2 is formed.

The container main unit 10 having the structure for assembly/disassembly remarkably increases workability for cleaning, and the inside of the container main unit 10 is surely cleaned, thereby more certainly preventing contamination from being possibly generated.

INDUSTRIAL APPLICABILITY

According to the invention of claim 1, an electric field having a cyclic distribution is formed by impressing a voltage upon the electrode pair in the container storing a sample having particles movably dispersed within a medium, diffraction grating formed by a density modulation of the particles are generated by applying a phoretic force generated by the electric field upon the particles, and the information upon the diffusion of the particles is obtained based upon a temporal change of the intensity of a diffracted light beam during the extinction process of the diffraction grating. As a result, compared with the conventional transient diffraction grating method, excitation light beams are not necessary, and adjustment of the optical axis thereof and the like are thus not necessary. Moreover, labeling of the particles to be measured is not necessary, and the particles can be measured and used again. Further, since the electrode teeth of the one electrode are inserted between the electrode teeth of the other electrode, namely, the electrode teeth of the respective electrodes are alternately arranged in parallel in the interdigital area, the width of the diffraction grating formed by the density modulation of the particles generated by the electric field generated by the electrode pair can be equal to the dimension of the interdigitated length of the electrode teeth, thereby increasing the component of the diffracted light beam from the diffraction grating formed by the density modulation of the particles of the diffracted light beam detected by the photodetector, resulting in achieving an increase of the sensitivity of the measurement.

According the inventions of claims 2 and 3, in addition to the above effects, since the grating interval of the diffraction grating formed by the density modulation of the particles can be made different from the grating interval of the diffraction grating formed by the electrode teeth, it is possible to detect the diffracted light beam coming from the diffraction grating formed by the density modulation of the particles in a direction different from the emerging direction of the diffracted light beam coming from the diffraction grating formed by the electrode teeth, thereby selectively detecting the diffracted light beam from the diffraction grating formed by the density modulation of the particles, resulting in achieving an increase of the S/N ratio of the measurement.

According the inventions there is provided the configuration that the electrode pair used to generate the electric field distribution in the container, thereby generating the diffraction grating formed by the density modulation of the particles is formed upon the structure which is a member independent of the container, and the structure is detachably installed upon the container, the clearing of the container and the electrodes is easy, the cleaning can be sufficiently carried out, and when different particles are measured with the same container/electrode pair, it is possible to surely prevent a measurement error caused by contamination due to a residual of particles used for the previous measurement.

The invention claimed is:

1. An optical measuring device comprising:
a container that stores a sample of particles movably dispersed within a medium;
an electric power supply that generates a voltage in a predetermined pattern including a DC, a frequency modulation, and a voltage modulation or in a pattern arbitrarily set;
an electrode pair that is provided within said container, and generates an electric field distribution regularly arranged within said container upon impression of the voltage by said electric power supply;
control means that control the impression of the voltage upon said electrode pair from said electric power supply to generate or extinguish diffraction grating formed by a density modulation of the particles generated by a phoretic force acting upon the particles within the sample within said container;
a light source that emits a light beam upon a generated region of said diffraction grating formed within said container; and
a photodetector that detects a diffracted light beam of said emitted light beam diffracted by said diffraction grating, wherein:
the particles within the sample are evaluated based upon a temporal change of an intensity of the diffracted light beam detected by said photodetector;
respective electrodes constituting said electrode pair comprise a comb-like electrode teeth that are parallel with each other, and a connecting portion that electrically connects said respective electrode teeth with each other; and
said respective electrodes are arranged such that while said electrode teeth of one of said respective electrodes are inserted between said electrode teeth of the other of said respective electrodes, said electrode teeth of said respective electrodes are separated by a constant interval, are parallel with each other, and are disposed alternately.

2. The optical measuring device according to claim 1, wherein at least one electrode of said electrode pair is covered with a thin film in order to prevent said electrode from reacting to the sample within said container.

3. The optical measuring device according to claim 1, wherein:
a part of a wall of said container is formed with a material which transmits the light beam from said light source;
said electrode pair is formed upon a structure which transmits the light beam from said light source; and
said structure is detachably installed at a position corresponding to said wall of said container which transmits the light beam from said light source.

4. The optical measuring device according to claim 3, wherein said structure upon which said electrode pair is formed is detachably installed upon said container so as to constitute the part of said wall of said container which transmits the light beam from said light source.

5. The optical measuring device according to claim 3, wherein said container comprises a structure of a plurality members detachably assembled with each other in addition to said structure upon which said electrode pair is formed.

6. The optical measuring device according to claim 3, wherein an engaging mechanism is formed between said container and said structure upon which said electrode pair is formed in order to maintain a mutual positional relationship thereof upon said structure upon which said electrode pair is formed being installed upon said container.

7. The optical measuring device according to claim 3, wherein, in order to maintain a mutual positional relationship between said structure upon which said electrode pair is formed and an optical path of the light beam emitted from said light source, there is formed an engaging mechanism between either of said structure or said container and a holding member that holds either of said structure or said container within the optical measuring device.

* * * * *